US010107754B2

(12) United States Patent
Suzuki et al.

(10) Patent No.: US 10,107,754 B2
(45) Date of Patent: Oct. 23, 2018

(54) BLOOD ANALYZER AND BLOOD ANALYZING METHOD

(71) Applicant: Sysmex Corporation, Kobe-shi, Hyogo (JP)

(72) Inventors: Yuhgi Suzuki, Kobe (JP); Munehisa Izuka, Kobe (JP); Konobu Kimura, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 15/250,168

(22) Filed: Aug. 29, 2016

(65) Prior Publication Data

US 2017/0059486 A1    Mar. 2, 2017

(30) Foreign Application Priority Data

Aug. 31, 2015   (JP) ................................ 2015-171209

(51) Int. Cl.
  *G01N 21/64*    (2006.01)
  *G01N 33/49*    (2006.01)
  (Continued)

(52) U.S. Cl.
  CPC ........... *G01N 21/6428* (2013.01); *G01N 1/30* (2013.01); *G01N 15/06* (2013.01); *G01N 15/147* (2013.01);
  (Continued)

(58) Field of Classification Search
  CPC ...... G01N 21/6428; G01N 21/47; G01N 1/30; G01N 15/06; G01N 15/147;
  (Continued)

(56) References Cited

U.S. PATENT DOCUMENTS

| 2004/0067575 | A1* | 4/2004 | Hanaoka | G01N 33/56905 435/252.3 |
| 2013/0046766 | A1* | 2/2013 | Shishido | G06F 17/30752 707/741 |
| 2015/0134263 | A1* | 5/2015 | Maeno | G01H 1/00 702/19 |

FOREIGN PATENT DOCUMENTS

| EP | 1 715 345 A1 | 10/2006 |
| JP | 2004-105027 A | 4/2004 |

(Continued)

OTHER PUBLICATIONS

CDC: "Normal Comparison of the Plasmodium Species Which Cause Human Malaria", Aug. 9, 2002, retrieved from the Internet on Jan. 20, 2017: https://www.cdc.gov/dpdx/resources/pdf/benchAids/malaria/Malaria_Comparison_p1-2.pdf, 2 pages.

(Continued)

*Primary Examiner* — Hina F Ayub
(74) *Attorney, Agent, or Firm* — Brinks Gilson & Lione

(57) ABSTRACT

A blood analyzer comprises a sample preparing part configured to prepare a measurement sample from a blood sample, an staining dye and diluent, a detecting part configured to detect the fluorescent light intensity and the scattered light intensity, an output part, and an analyzing part configured to identify the population including red blood cells infected by ring-form malaria parasite based on the fluorescent light intensity and the scattered light intensity, and output to the output part the information relating to infection of *Plasmodium falciparum* based on the scattered light distribution of particles associated with the identified population that includes red blood cells infected by the ring-form malaria parasite.

16 Claims, 15 Drawing Sheets

(51) Int. Cl.
*G01N 33/50* (2006.01)
*G01N 33/58* (2006.01)
*G01N 1/30* (2006.01)
*G01N 15/06* (2006.01)
G01N 15/00 (2006.01)
G01N 15/10 (2006.01)
G01N 15/14 (2006.01)
G01N 21/47 (2006.01)

(52) U.S. Cl.
CPC ......... *G01N 21/47* (2013.01); *G01N 33/4915* (2013.01); *G01N 33/5091* (2013.01); *G01N 33/5094* (2013.01); *G01N 33/582* (2013.01); G01N 2001/302 (2013.01); G01N 2015/0065 (2013.01); G01N 2015/0073 (2013.01); G01N 2015/0693 (2013.01); G01N 2015/1037 (2013.01); G01N 2015/1402 (2013.01); G01N 2015/1477 (2013.01); G01N 2015/1486 (2013.01); G01N 2015/1488 (2013.01); G01N 2015/1493 (2013.01); G01N 2021/4707 (2013.01); G01N 2021/6439 (2013.01); G01N 2201/0612 (2013.01); G01N 2201/12 (2013.01); G01N 2333/445 (2013.01)

(58) Field of Classification Search
CPC ........... G01N 33/4915; G01N 33/5091; G01N 33/5094; G01N 33/582; G01N 2001/302; G01N 2015/0065; G01N 2015/0073; G01N 2015/0693; G01N 2015/1037; G01N 2015/1402; G01N 2015/1477; G01N 2015/1486; G01N 2015/1488; G01N 2015/1493; G01N 2021/4707; G01N 2021/6439; G01N 2201/0612; G01N 2201/01

USPC .......................................................... 356/39
See application file for complete search history.

(56) References Cited

FOREIGN PATENT DOCUMENTS

| JP | 2004-141150 | 5/2004 |
|---|---|---|
| JP | 2006-304774 | 11/2006 |
| WO | WO 2009/136570 | 11/2009 |
| WO | WO 2009/136573 | 11/2009 |

OTHER PUBLICATIONS

David C. Warhurst, "Resistance to Antifolates in Plasmodium Falciparum, the Causative Agent of Tropical Malaria," Science Progress, vol. 85, No. 1, dated Feb. 15, 2002, pp. 89-111, XP055447823, GB.

R. Louise Krauth-Siegel et al., "Glutathione Reductase and Glutamate Dehydrogenase of Plasmodium Falciparum, the Causative Agent of Tropical Malaria," Eur. J. Biochem, vol. 235, Issue 1-2, dated Jan. 1, 1996, pp. 354-350, XP055447831, retrieved from the Internet: URL:http://onlinelibrary.wiley.com/doi/10.1111/j.1432-1033.1996.00345.x/full [retrieved on Feb. 5, 2018].

R. Luise Krauth-Siegel et al., "Dithiol Proteins as Guardians of the Intracellular Redox Milieu in Parasites: Old and New Drug Targets in Trypanosomes and Malaria-Causing Plasmodia," Angewandte Chemie International Edition, vol. 44, No. 5, dated Jan. 21, 2005, pp. 690-715, XP055447836.

* cited by examiner

BLOOD ANALYZER AND BLOOD ANALYZING METHOD

CROSS REFERENCE TO RELATED APPLICATIONS

This application claims priority from prior Japanese Patent Application No. 2015-171209, filed on Aug. 31, 2015, entitled "BLOOD ANALYZER AND BLOOD ANALYZING METHOD", the entire contents of which are incorporated herein by reference.

FIELD OF THE INVENTION

The present invention relates to a blood analyzer and blood analyzing method for analyzing malaria infected blood samples using measurement samples prepared from blood.

BACKGROUND

Japanese Patent Application Publication No. 2006-2304774 discloses a method for detecting red blood cells infected with the malaria parasite (referred to as 'malaria infected red blood cells' below). In this detection method, a measurement sample is prepared by mixing a blood sample with reagent that can partially lyse the cell membrane of red blood cells so that a staining dye holding malaria parasite inside and that contains a stain that stains DNA more strongly than RNA, then the measurement sample is introduced to a flow cytometric flow cell, the measurement sample flowing through the flow cell is irradiated by light, the scattered light and fluorescent light given off by the measurement sample are detected, and a scattergram is created with the scattered light intensity and fluorescent light intensity as the two axes.

In red blood cells infected by the ring-form type of malarial parasite, there are red blood cells containing a single malarial parasite (referred to as 'single-ring form' below) and red blood cells containing two or more malarial parasites (referred to as multi-ring form' below), with different amounts of DNA contained in the single-ring form and multi-ring form. Also, in *falciparum* malaria, the proportion of multi ring-form tends to be high. Focusing on this, the detection method disclosed in patent reference 1, separately detects single-ring form and multi-ring form that appear in regions of different fluorescent light intensities in a scattergram, and determines whether it is *falciparum* malaria based on the number of dots (number of cells) present in the multi-ring form region.

Sometimes the multi-ring form may not appear in *falciparum* malaria. In the detection method disclosed in Patent reference 1, there is a possibility that an accurate determination may not be made for a measurement sample using the number of multi-ring forms. It is therefore desirable to improve the determination accuracy regarding whether a measurement sample is infected by *Plasmodium falciparum*.

SUMMARY OF THE INVENTION

The scope of the present invention is defined solely by the appended claims, and is not affected to any degree by the statements within this summary.

The blood analyzer of a first aspect of the invention is provided with a sample preparing part, detecting part, output part, and analyzing part. The sample preparing part prepares a measurement sample from a blood sample, staining dye that stains nucleic acid, and diluent that contracts red blood cells. The detecting part detects the fluorescent light intensity and scattered light intensity given off from the measurement sample irradiated with light. The analyzing part identifies a population containing red blood cells infected by ring-form malarial parasite based on the fluorescent light and scattered light detected by the detecting part, and outputs to the output part information relating to infection of *Plasmodium falciparum* based on the scattered light intensity of particles belonging to the group identified as containing red blood cells infected by ring-form malarial parasite.

The blood analyzing method of a second aspect of the invention irradiates light on a measurement sample prepared from a blood sample, a staining dye to stain nucleic acid, and diluent to contract red blood cells, and detects the fluorescent light and scattered light obtained by irradiating light on the measurement sample. The blood analyzing method identifies a population containing red blood cells infected by ring-form malarial parasite based on the detected fluorescent light intensity and scattered light intensity. The blood analyzing method also makes a determination regarding infection by *Plasmodium falciparum* based on the distribution of scattered light intensity of particles belonging to a group containing red blood cells infected by ring-form malarial parasite.

According to the invention, whether a blood sample is infected by *Plasmodium falciparum* can be more accurately determined.

DETAILED DESCRIPTION OF THE PREFERRED EMBODIMENTS

The embodiment is described in terms of a blood analyzer that identifies a population containing malaria infected red blood cells based on the fluorescent light intensity and forward scattered light intensity produced when light is irradiated on a measurement sample prepared from a blood sample and reagent, and determines whether the malarial parasite infecting the red blood cells is *Plasmodium falciparum*.

Blood Analyzer Structure

Figure 1:
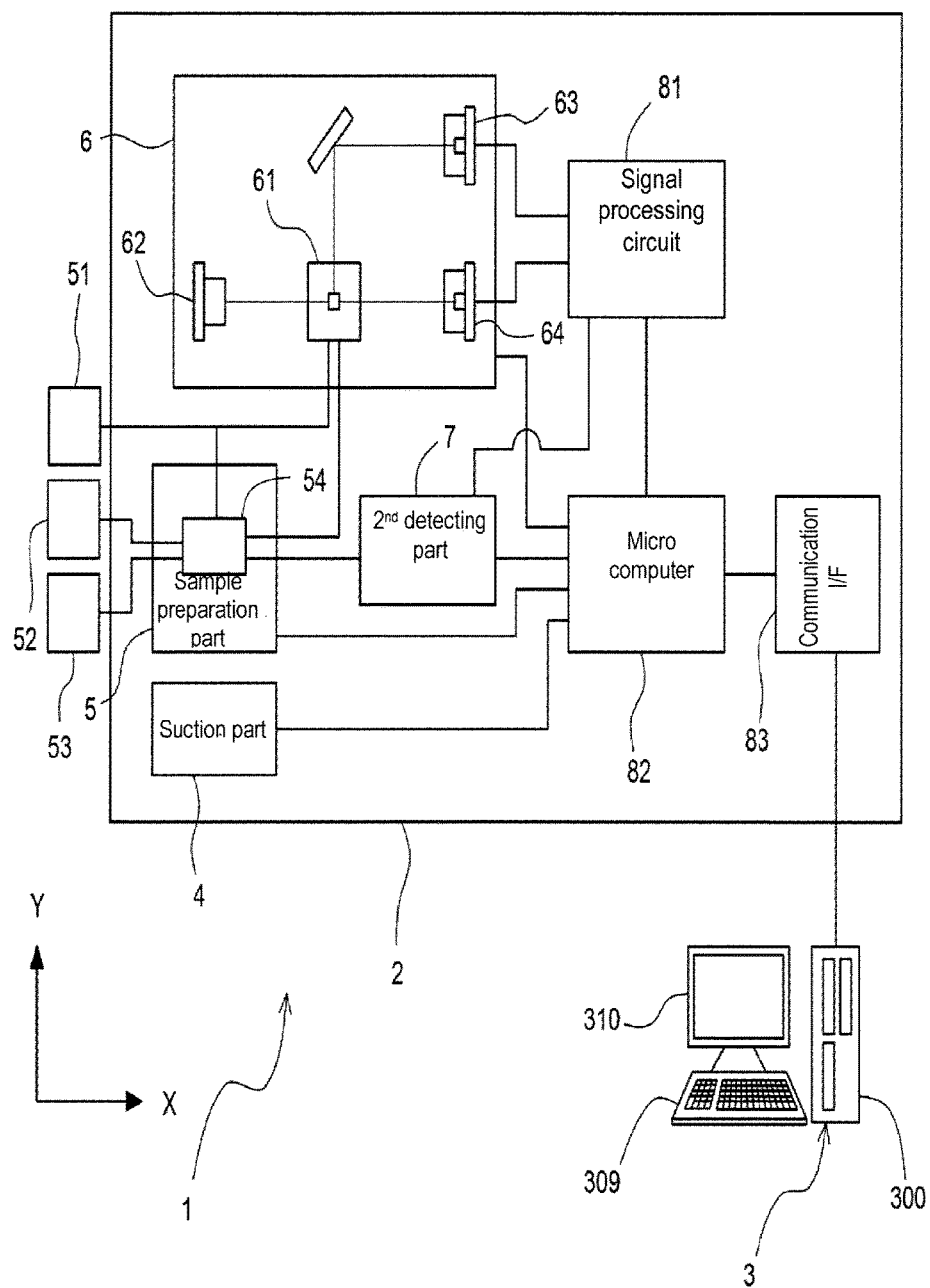
FIG. 1 is a schematic view showing the structure of the blood analyzer of an embodiment.

The structure of the blood analyzer is described referring to FIG. 1. The blood cell analyzer 1 includes a measuring part 2 and an analyzing part 3. The measuring part 2 receives a blood sample, prepares a measurement sample from the blood sample, and performs optical measurements of the measurement sample. The analyzing part 3 processes the measurement data obtained by the measurement performed by the measuring part 2, and outputs analysis results of the blood sample.

The measuring part 2 includes a suction part 4, sample preparing part 5, optical detecting part 6, second detecting part 7, signal processing circuit 81, microcomputer 82, and communication interface 83.

The suction part 4 has a suction tube that is not shown in the drawing, and suctions the blood sample held in a test tube through the suction tube.

The sample preparing part 5 has a reaction tank 54 that is connected to reagent containers 51, 52, and 53. The reagent container 52 contains a first diluent that contracts red blood cells. The reagent container 53 contains a staining reagent that contains staining dye to stain nucleic acid. The reagent container 51 contains a second diluent. The suction part 4 raises the suction tube above the reaction tank 54, and discharges the suctioned blood sample into the reaction tank 54. The blood sample, first diluent, and staining reagent are mixed in the reaction tank 54 to prepare the measurement sample. The measurement sample is used in the measurements of white blood cells and malaria infected red blood cells. The blood sample suctioned by the suction part 4 is mixed with the second diluent in the reaction tank 54 to prepare a second measurement sample. The second measurement sample is used in the measurement of red blood cells.

The first diluent held in the reagent container 52 is described. The first diluent contains two types of surface active agents that have different hemolytic power. Specifically, the first diluent contains 2.95 mM lauryl trimethyl ammonium chloride as cationic surface active agent, and 1.11 mM stearyl trimethyl ammonium chloride as a cationic surface active agent. Stearyl trimethyl ammonium chloride has stronger hemolytic power than lauryl trimethyl ammonium chloride. The surface active agents are not limited to the above insofar as the two types of surface active agents have different hemolytic power. The first diluent also contains 2.90 mM PBC-44 as a nonionic surface active agent, 20 mM ADA, an appropriate amount of NaCl, and 1 L purified water. ADA has a pH of 6.1. The first diluent also has a pH of 5.0 or greater but not more than 7.0. The osmotic pressure of the first diluent is preferably 200 mOsm/kg.H2O or more to contract the blood cells. Specifically, the osmotic pressure of the first diluent is 200 mOsm/kg.H2O or greater but not more than 300 mOsm/kg.H2O.

The second diluent differs from the first diluent that contracts red blood cells, and is a diluent used in the measurement of red blood cells by a sheath flow-DC detection method. The second diluent is also used as a sheath fluid in the measurement of blood cells by a flow cytometric method. The first diluent is not used as a sheath fluid.

The staining reagent held in the reagent container 53 is described. The staining reagent contains staining dye (Hoechst 34580). The concentration of staining dye in the staining reagent is preferably 0.3 μM or greater but less than 0.6 μM, specifically, 0.45 μM in this case. The concentration of staining dye in the measurement sample also is preferably 0.15 μM or greater but not more than 1.0 μM. The chemical formula of Hoechst 34580 is shown below.

[Chemical Formula 1]

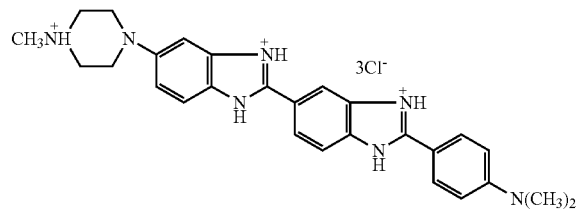

Note that the measurement sample also may be prepared by mixing blood sample and one reagent that contains staining dye and the first diluent that contracts red blood cells without separating the first diluent and staining reagent.

The optical detecting part 6 is used to measure white blood cells and malaria infected red blood cells by flow cytometric method. The optical detecting part 6 includes a flow cell 61, light source 62, and detectors 63 and 64. The flow cell 61 receives the measurement sample prepared by the sample preparing part 5 and the second diluent contained in reagent container 51. The flow cell 61 forms a flow in which the measurement sample is encapsulated in sheath fluid, that is, the second diluent.

The light source 62 is a semiconductor laser light source that emits blue-violet laser light with a wavelength of 405 nm toward the flow cell 61.

The detectors 63 and 64 detect the light given off from the measurement sample when the measurement sample in the flow cell 61 is irradiated by light. Avalanche photodiodes may be used for the detectors 63 and 64. In the following description, the direction connecting the light source 62 and the flow cell 61 is referred to as the "X direction", and the direction perpendicular to the X direction is referred to as the "Y direction". The detector 63 can detect fluorescent light given off from the measurement sample through a mirror positioned on the Y direction side of the flow cell 61. The detector 64 is positioned on the X direction side of the flow cell 61. More specifically, the detector 64 is positioned on the opposite side of the light source 62 so as to interpose the flow cell 61 therebetween. The detector 63 and the detector 64 can detect forward scattered light given off from the measurement sample.

Note that other scattered light, such as side scattered light, backward scattered light and the like also may be detected instead of forward scattered light.

The detectors 63 and 64 respectively output analog signals representing the intensity of the received light. The analog signals output from the detector 63 are referred to as "fluorescent light signals", and the analog signals output from the detector 64 are referred to as "forward scattered light signals" below.

The second detecting part 7 is used to measure red blood cells by a sheath flow-DC detection method. The second detecting part 7 receives the second measurement sample from the sample preparing part 5. The second detecting part 7 includes a sheath flow cell that is not shown in the drawings, and a voltage is applied to the second measurement sample flowing through the sheath flow cell. When a blood cell passes through the sheath flow cell, the voltage is changed by the electrical resistance of the blood cell. The second detecting part 7 detects the blood cell by capturing the change in voltage, hence detecting the electrical resistance. The second detecting part 7 outputs an analog signal representing the voltage.

The signal processing circuit 81 performs signal processing of the analog signals output from the detectors 63 and 64, and the second detecting part 7. The signal processing circuit 81 extracts the pulse peak value included in the fluorescent light signal and forward scattered light signal as characteristic parameters. Below, the peak value of the fluorescent light signal is referred to as the "fluorescent light intensity", and the peak value of the forward scattered light signal is referred to as the "forward scattered light intensity". The signal processing circuit 81 extracts the peak values of the output signals of the second detecting part 7 as red blood cell detection data.

The microcomputer 82 controls the suction part 4, sample preparing part 5, optical detecting part 6, second detecting part 7, signal processing circuit 81, and communication interface 83.

The communication interface 83 is connected to the analyzing part 3 by a communication cable. The measuring part 2 performs data communication with the analyzing part 3 through the communication interface 83. The communication interface 83 transmits measurement data containing each characteristic parameter to the analyzing part 3 when a blood sample is measured.

Figure 2:
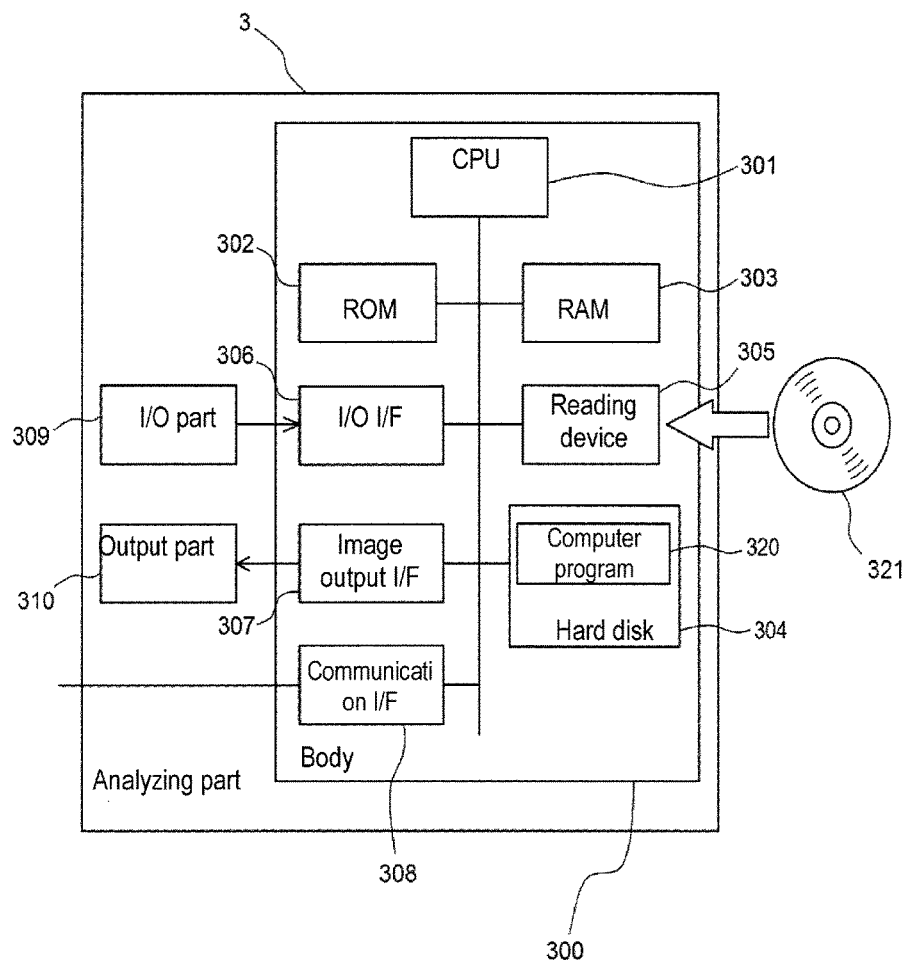
FIG. 2 is a block diagram showing the structure of the analyzing part.

The structure of the analyzing part 3 is described referring to FIG. 2. The analyzing part 3 includes a body 300, input part 309, and output part 310. The body 300 has a CPU (Central Processing Unit) 301, ROM (Read Only Memory) 302, RAM (Random Access Memory) 303, hard disk 304, reading device 305, Input/output (I/O) interface 306, image output interface 307, and communication interface 308. In the embodiment, a display that displays images is used as the output part 310. However, a printer that outputs to paper or the like by printing also may be used as the output part 310.

The CPU 301 executes a computer program stored in the ROM 302, and computer program loaded in the RAM 303. The RAM 303 is used when reading a computer program recorded in ROM 302 and hard disk 304. The RAM 303 also is used as a work area of the CPU 301 when the CPU 301 executes a computer program.

A computer program 320 for analyzing measurement data received from the measuring part 2 and outputting the analysis results is installed on the hard disk 304.

The reading device 305 is a floppy disk drive, CD-ROM drive, DVD-ROM drive or the like, capable of reading computer programs and data recorded on a portable recording medium 321. The computer program 320 that is stored on the portable recording medium 321 enables a computer to function as the analyzing part 3. The computer program 320 is read from the portable recording medium 321 and installed on the hard disk 304.

The input part 309 is connected to the I/O interface 306. The output part 310 is connected to the image output interface 307. The communication interface 308 is connected to the communication interface 83 of the measuring part 2.

Blood Analyzer Operation

Figure 3:
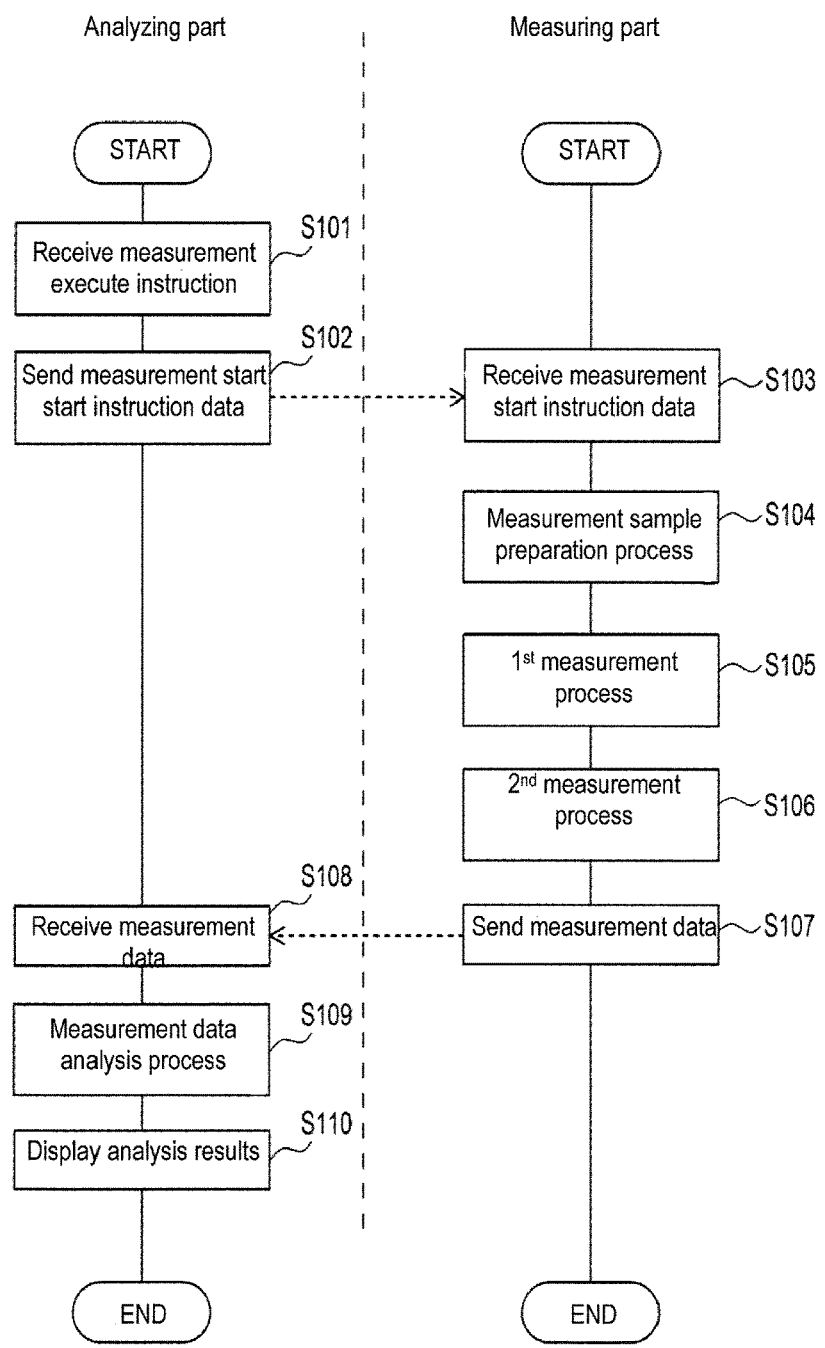
FIG. 3 is a flow chart showing the operation flow of the blood analyzer of the embodiment.

The operation of the blood analyzer 1 is described referring to FIG. 3.

First, the CPU 301 of the analyzing part 3 receives instruction to execute measurement from a user through the input part 309 (step S101). When the measurement execution instruction is received, the CPU 301 sends instruction data directing that measurement should start to the measuring part 2 (step S102), and the measuring part 2 receives the instruction data (step S103). The microcomputer 82 executes a measurement sample preparation process (step S104), executes a first measurement process (step S105), and executes a second measurement process (step S106).

Figure 4:
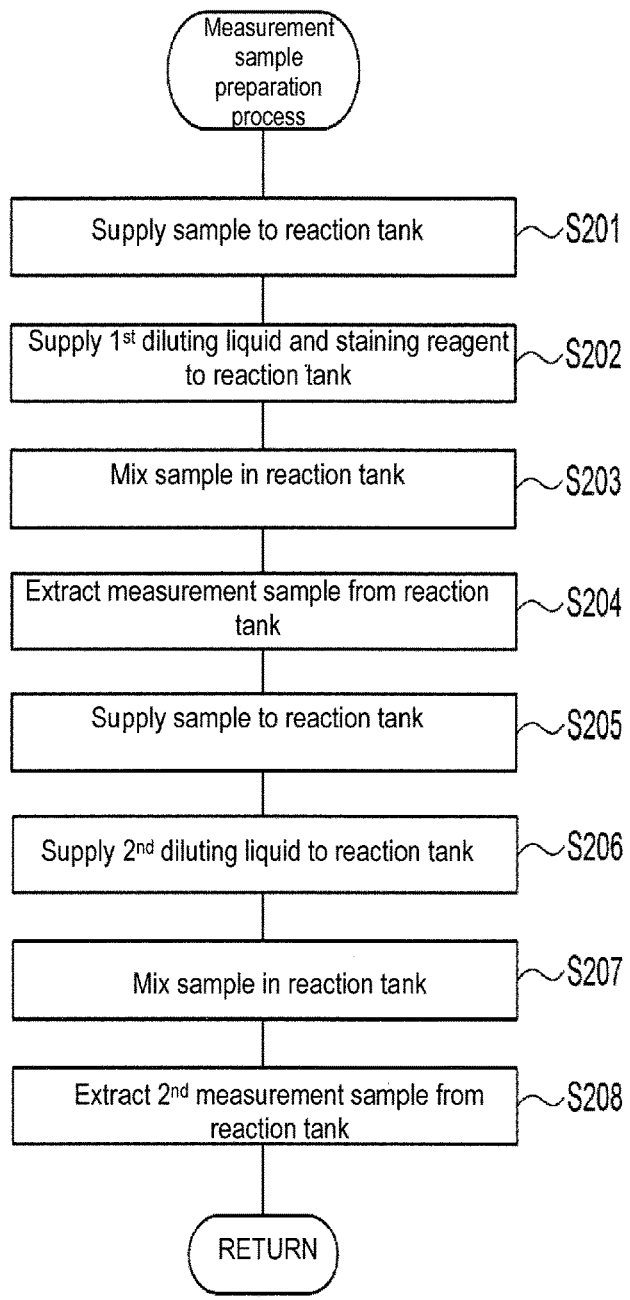
FIG. 4 is a flow chart showing the sequence of the measurement sample preparation process.

The measurement sample preparation process is described referring to FIG. 4. The microcomputer 82 controls the suction part 4 to supply a predetermined amount, for example, 17 μL, of blood sample to the reaction tank 54 (step S201). Then, the microcomputer 82 controls the sample preparing part 5 to supply a predetermined amount, for example, 1 mL, of the first diluent from the reagent container 52 to the reaction tank 54, and supply a predetermined amount, for example, 20 μL, of staining dye from the reagent container 53 to the reaction tank 54 (step S202).

The reaction tank 54 it heated to a predetermined temperature by a heater. The mixture within the reaction tank 54 is mixed in the heated condition. The measurement sample is prepared in the reaction tank 54 through the operations of steps S201 to S203. The microcomputer 82 controls the sample preparing part 5 to supply the measurement sample from the reaction tank 54 to the optical detecting part 6 (step S204).

The microcomputer 82 controls the suction part 4 to suction a predetermined amount of blood sample from the test tube, and supply a predetermined amount, for example, 4 μL, of blood sample to the reaction tank 54 (step S205). Then, the microcomputer 82 controls the sample preparing part 5 to supply a predetermined amount, for example, 2000 μL, of the second diluent from the reagent container 51 to the reaction tank 54 (step S206).

Next, the sample preparing part 5 mixes the mixture within the reaction tank 54 (step S207). The second measurement sample is prepared in the reaction tank 54 through the operations of steps S205 to S207. The microcomputer 82 controls the sample preparing part 5 to supply the second measurement sample from the reaction tank 54 to the second detecting part 7 (step S208).

When the process of step S208 is completed, the microcomputer 82 returns the process to the main routine.

Refer again to FIG. 3. In the first measurement process the measurement sample is measured by the optical detecting part 6. The sample preparing part 5 supplies the measurement sample together with the sheath fluid to the flow cell 61. The light source 62 irradiates light on the measurement sample flowing through the flow cell 61.

When the measurement sample flows through the flow cell 61, white blood cells, platelet aggregation, and red blood cells sequentially pass through the flow cell 61. In this case, "platelet aggregation" is the aggregation of two or more platelets. When red blood cells include malaria infected red blood cells, the malarial parasite is inside the malaria infected red blood cell. Red blood cells in the measurement sample are contracted by the action of the first diluent.

Malaria infected red blood cells are contracted by the first diluent while maintaining the malarial parasite in the interior of the cell. The malarial parasite also is stained by the staining reagent due to the presence of a nucleus. Since white blood cells also contain a nucleus, white blood cells are also stained by the staining reagent. Since red blood cells that are not infected by malarial parasite (referred to as "normal red blood cells" below) and aggregated platelets do not contain a nucleus, they are scarcely stained by the staining reagent.

When a blood cell is irradiated with light, the blood cell (white blood cell, platelet aggregation, red blood cell) gives off fluorescent light and forward scattered light. The fluorescent light given off from the blood cell is detected by the detector 63. The forward scattered light given off by the blood cell is detected by the detector 64.

The detectors 63 and 64 respectively output electrical signals that correspond to the level of received light as fluorescent light signals and forward scattered light signals. The signal processing circuit 81 extracts the fluorescent light intensity from the fluorescent light signal, and extracts the forward scattered light intensity from the forward scattered light signal.

In the second measurement process the second measurement sample is measured by the second detecting part 7. The second detecting part 7 applies a voltage to the second measurement sample that is flowing through the sheath flow cell, and outputs analog signals representing the voltage to the signal processing circuit 81. When a red blood cell passes through the sheath flow cell, the voltage is changed by the electrical resistance of the red blood cell. The signal processing circuit 81 captures the change of electrical resistance through signal processing, and detects the red blood cell. The signal processing circuit 81 converts the output signals of the second detecting part 7 as red blood cell detection data.

After the second measurement process, the microcomputer 82 sends the measurement data containing each characteristic parameter to the analyzing part 3 (step S107).

The analyzing part 3 receives the measurement data (step S108). Thereafter, the CPU 301 executes the measurement data analysis process, generates analysis results of the measurement sample, and stores the analysis results on the hard disk 304 (step S109).

Figure 5:
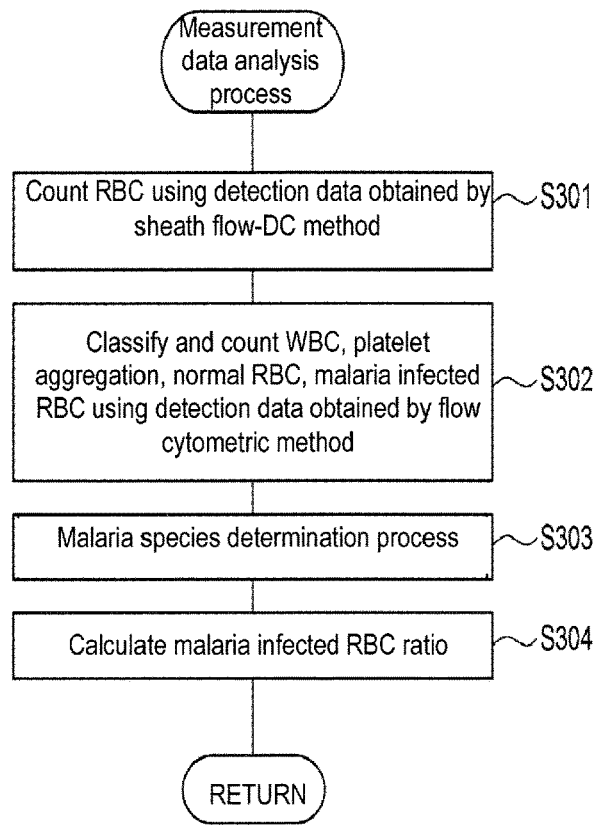
FIG. 5 is a flow chart showing the sequence of the measurement data analysis process.

The measurement data analysis process is described referring to FIG. 5. When the measurement data analysis process starts, the CPU 301 first counts the red blood cells using the detection data of red blood cells included in the measurement data (step S301).

Red blood cells also may be counted using the forward scattered light intensity included in the measurement data rather than by the sheath flow-DC method. Red blood cells are contracted by the first diluent. The forward scattered light intensity is a characteristic parameter that reflects the size of the blood cell, and the forward scattered light intensity of contracted red blood cells take a specific range of values. Therefore, particles that have a forward scattered light intensity within the specific range in which red blood cells appear also may be designated as red blood cells and counted. Red blood cells also can be detected using the pulse width and pulse area of the forward scattered light rather than using the forward scattered light intensity. Red blood cells also can be detected by detecting the side scattered light and using the pulse peak value, pulse width, or pulse area of the side scattered light rather than using the forward scattered light.

Then, the CPU 301 classifies and respectively counts the white blood cells, platelet aggregation, normal red blood cells, and malaria infected red blood cells based on the fluorescent light intensity and forward scattered light intensity included in the measurement data (step S302). Note that since normal red blood cells are excluded from the particles being analyzed in this process, particles for which the fluorescent light intensity is less than a predetermined threshold value are excluded. The majority of normal red blood cells are not adequately stained by the staining dye and either do not give off fluorescent light or give off weak fluorescent light. Therefore, most normal red blood cells can be excluded by excluding from analysis those particles for which the fluorescent light intensity is less than a predetermined threshold value. However, some normal red blood cells that give off fluorescent light, such as reticulocytes, cannot be excluded. In step S302, normal red blood cells that cannot be excluded in this way are detected and distinguished form other blood cells.

Figure 6:
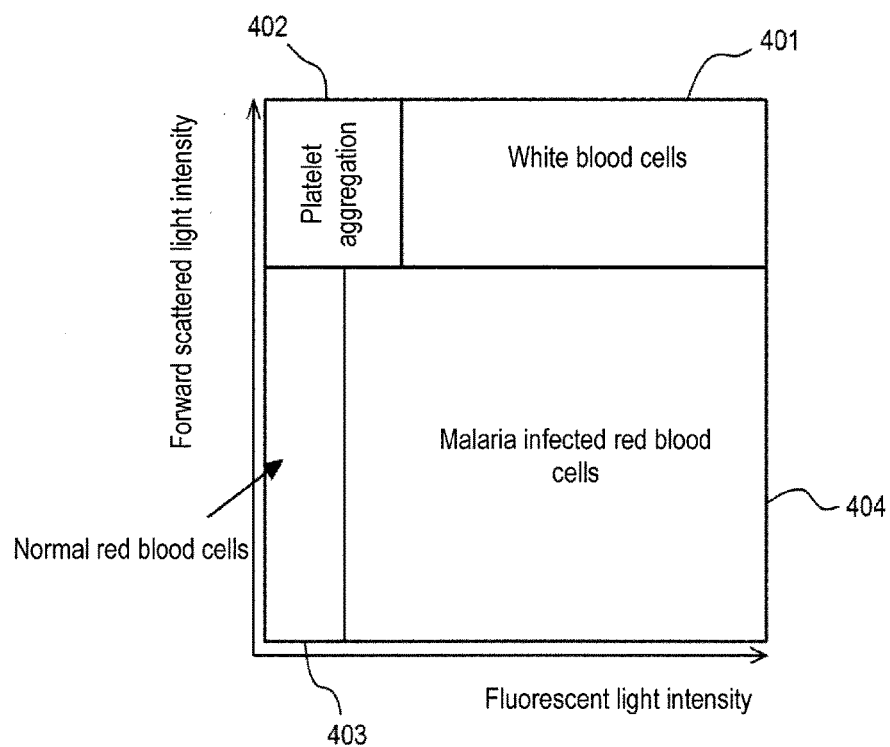
FIG. 6 illustrates the appearance region of each particle group of white blood cells, platelet aggregation, normal red blood cells, and malaria infected red blood cells in a scattergram in which the forward scattered light intensity is plotted on the vertical axis and the fluorescent light intensity is plotted on the horizontal axis.

The classification of white blood cells, platelet aggregation, normal red blood cells, and malaria infected red blood cells is described referring to FIG. 6. In the scattergram of FIG. 6, the vertical axis represents the forward scattered light and the horizontal axis represents the fluorescent light.

The population including white blood cells generally appears in region 401 in which the forward scattered light intensity and fluorescent light intensity is greater. The population including platelet aggregation generally appears in region 402 in which the forward scattered light intensity is the same as that of region 401 of the population including white blood cells, but the fluorescent light intensity is less than that of region 401. Normal red blood cells are strongly contracted by the first diluent. Although normal red blood cells have a fluorescent light intensity less than the predetermined threshold value and, therefore, are excluded from analysis as described above, unexcluded normal red blood cells also may be inadequately stained by the staining reagent and give off only weak fluorescent light. Therefore, the population including normal red blood cells contracted by the first diluent generally appears as normal red blood cells in region 403 in which the forward scattered light intensity is less than that of region 401 of the population including white blood cells, and the fluorescent light intensity is less than that of region 401.

Malaria infected red blood cells are strongly contracted by the first diluent, and also are stained by the staining reagent because the malaria parasite held within the cell has a nucleus. Therefore, the population including malaria infected red blood cells generally appears in region 404 in which the forward scattered light intensity is less than that of region 401 of the population including white blood cells, and the fluorescent light intensity is greater than that of region 403 of the population including normal red blood cells.

In the process of step S302, the CPU 301 combines the particle size distribution of the forward scattered light intensity and the particle size distribution of the fluorescent light intensity in the measurement data, and identifies the population including white blood cells, population including platelet aggregation, population including normal red blood cells, and population including malaria infected red blood cells. More specifically, the CPU 301 identifies a seventh particle group in which the forward scattered light intensity is less than that of the first particle group of the population including white blood cells, and the fluorescent light intensity is greater than that of the second particle group of the population including normal red blood cells. The seventh particle group is a population including malaria infected red blood cells. Note that the particle group in which the forward scattered light intensity and fluorescent light intensity is less than that of a specific particle group is referred to as a small particle group in which the forward scattered light intensity and fluorescent light intensity is at least partially less than that of a specific particle group. Moreover, the particle group in which the forward scattered light intensity and fluorescent light intensity is greater than that of a specific particle group is referred to as a large particle group in which the forward scattered light intensity and fluorescent light intensity is at least partially greater than that of a specific particle group. Further, the particle group in which the forward scattered light intensity and fluorescent light intensity is the same level as that of a specific particle group is referred to as a similar particle group in which the forward scattered light intensity and fluorescent light intensity is at least partially the same level as that of a specific particle group.

Refer again to FIG. 5. The CPU 301 executes the malaria type determination process (step S303).

Figure 7:
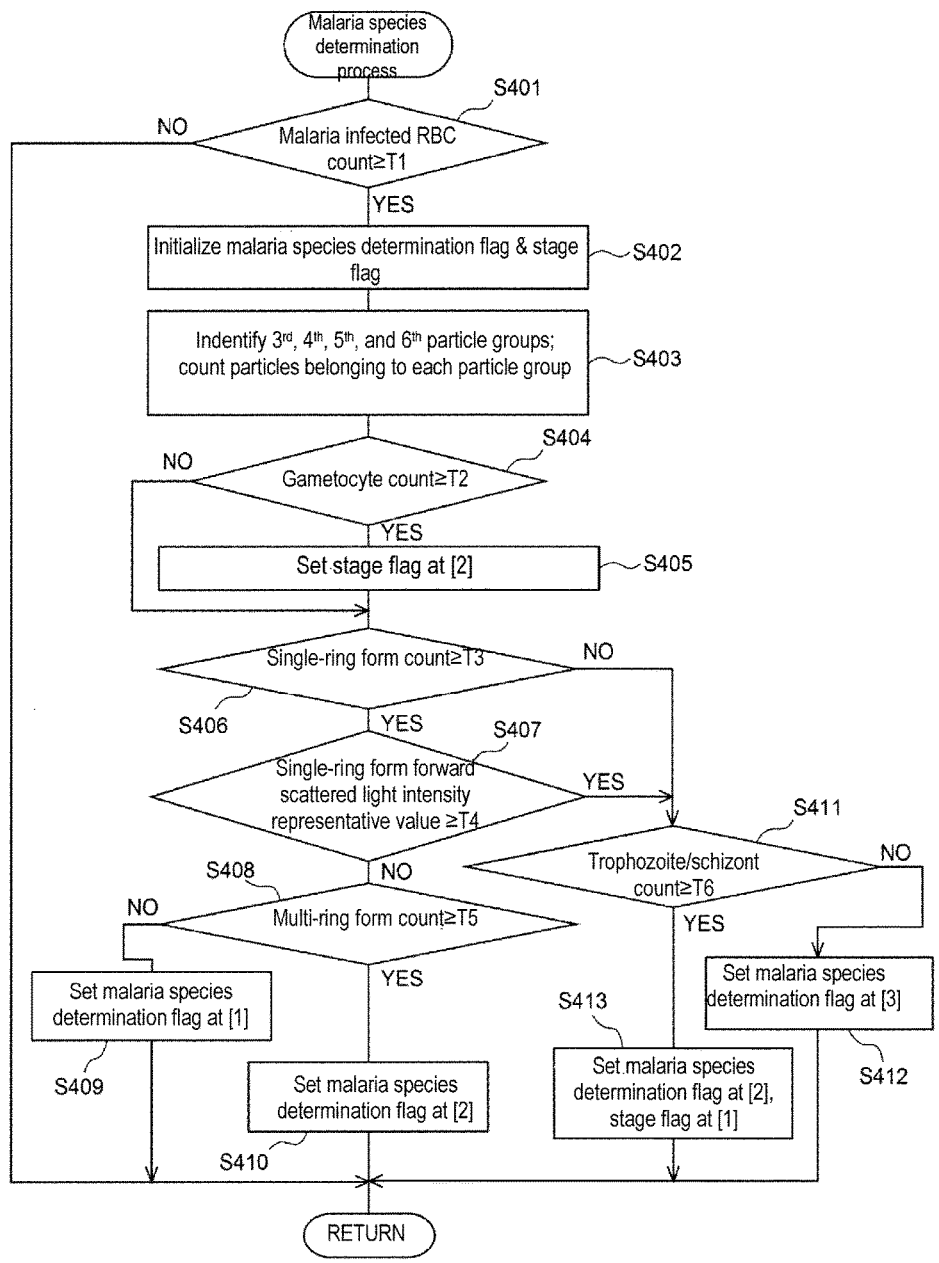
FIG. 7 is a flow chart showing the sequence of the malaria type determination process.

The malaria type determination process is described referring to FIG. 7. The malaria type determination process is a process for determining whether the blood sample is suspected of being infected by *Plasmodium falciparum*, or whether the blood sample is suspected of being infected by another type of malarial parasite other than *falicparum* malaria (referred to as "other type" below).

The CPU 301 determines whether the number of malaria infected red blood cells is a predetermined value T1 or greater (step S401). In this case T1 is a numerical value that permits a determination that malaria infected red blood cells are not present, when considering noise if the number of malaria infected red blood cells is less than T1. When the number of malaria infected red blood cells is less than T1 (step S401: NO), it can be determined that the blood sample is not infected by malaria parasite. In this case, the CPU 301 ends the malaria type determination process, and returns to the measurement data analysis process.

When the number of malaria infected red blood cells is T1 or greater (step S401: YES), it can be determined that there is a possibility the blood sample is infected by malaria parasite. In this case, the CPU 301 moves the process to step S402.

The red blood cell internal type life cycle of the malaria parasite begins when one type of malaria parasite, a merozoite, invades the red blood cell. In the red blood cell internal type life cycle the form of the malaria parasite sequentially changes to ring form, trophozoite, and schizont. The schizont divides into a plurality of merozoites, which then rupture the red blood cell. In this way numerous merozoites are released into the blood. Merozoites then invade the next red blood cell and the red blood cell internal type life cycle begins again. This cycle repeats and the malaria parasites multiply.

Some of the merozoites released into the blood differentiate to male and female gametocytes. When a mosquito sucks the blood of an infected person, the gametocytes are introduced into the body of the mosquito and the mosquito hosts the malaria parasite.

In step S402, the CPU 301 respectively sets the initial values to [0] for the malaria species determination flag related to the species of malaria parasite that possibly infects the blood sample, and the stage flag related to the stage of the malaria parasite that possibly infected the blood sample. The malaria species determination flag and the stage flag are provided in specified regions of the RAM 303.

A malaria species determination flag set at [0] indicates a low possibility that the blood sample is infected by malaria parasite. A malaria species determination flag set at [1] indicates that the blood sample is suspected of infection by *Plasmodium falciparum*. A malaria type determination flag set at [2] indicates a high possibility that the blood sample is infected by *Plasmodium falciparum*. Note that suspicion of infection by *Plasmodium falciparum* indicates a likely infection by *Plasmodium falciparum*, although the possibility cannot be said to be high.

A malaria species determination flag set at [3] indicates that the blood sample is suspected of infection by another species of malaria parasite. A malaria species determination flag set at [4] indicates a high possibility that the blood sample is infected by another species of malaria parasite.

A stage flag set at [0] indicates a low possibility of the presence of trophozoites and schizonts, and gametocytes. A stage flag set to [1] indicates a high possibility of the presence of trophozoites and schizonts in the blood sample. A stage flag set at [2] indicates a high possibility of the presence of gametocytes.

The CPU 301 then identifies a third particle group of a population including single-ring form, a fourth particle group of a population including multi-ring form, a fifth particle group of a population including red blood cells that contain trophozoites and schizonts (referred to as "trophozoite/schizont" below), and a sixth particle group of a population including gametocytes, and counts the particles belonging to each particle group (step S403).

Figure 8:
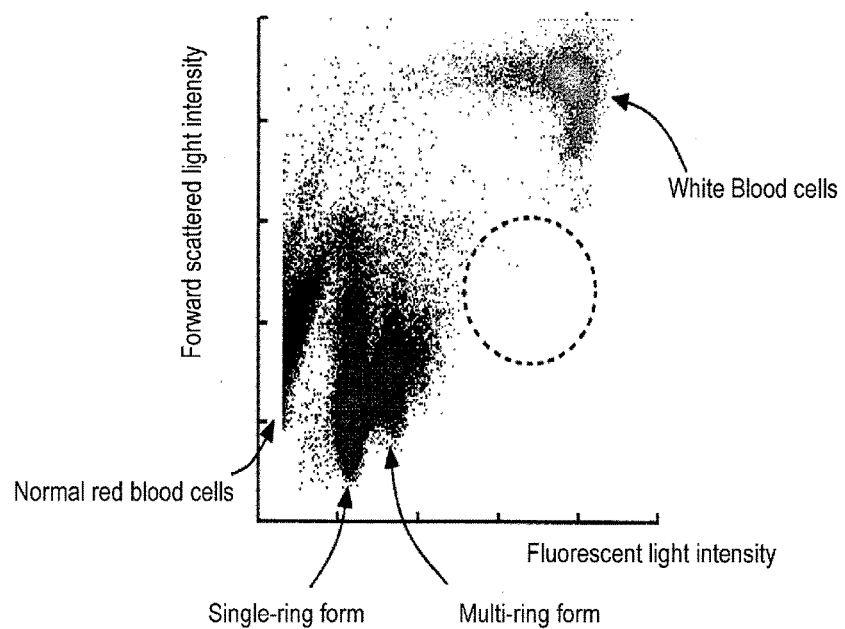
FIG. 8 shows an example of a scattergram of a blood sample infected by *Plasmodium falciparum*.
Figure 9:
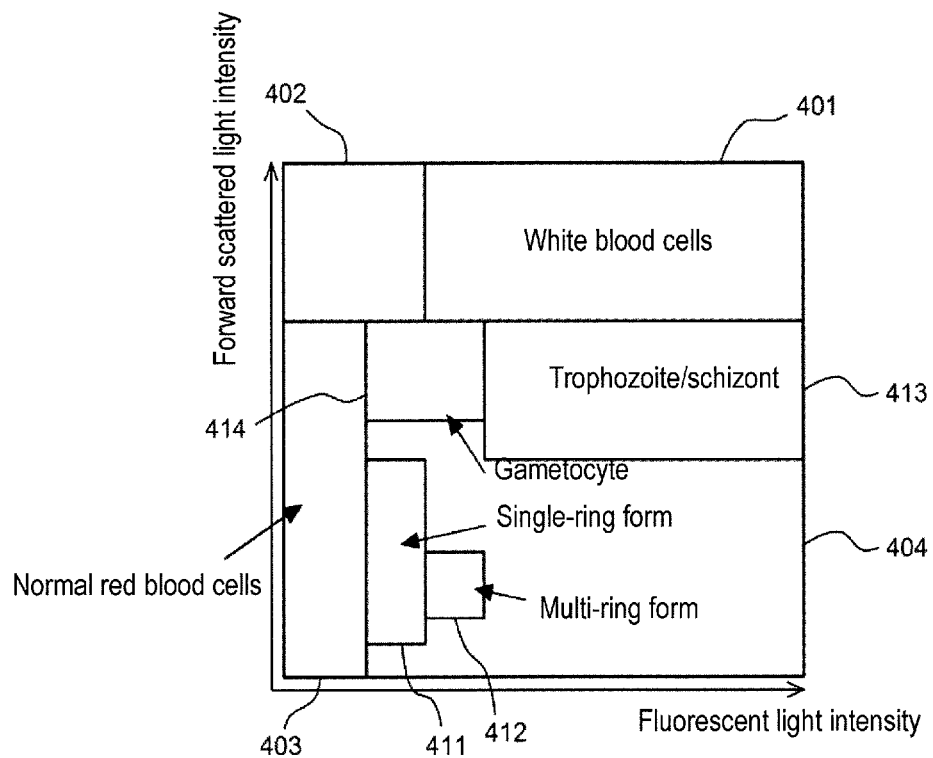
FIG. 9 illustrates the appearance region of each particle group of white blood cells, platelet aggregation, normal red blood cells, single-ring forms, multi-ring forms, trophozoites, schizonts, and gametocytes in a scattergram with the forward scattered light intensity plotted on the vertical axis and the fluorescent light intensity plotted on the horizontal axis.

The process of step S403 is specifically described below. FIG. 8 shows an example of a scattergram in which a population including single-ring form, and a population including multi-ring form appear. As shown in FIG. 8, the population including single-ring form has a forward scattered light intensity that is less than that of the population including white blood cells, and the fluorescent light intensity is less than that of the population including white blood cells. The population including single-ring form also has a fluorescent light intensity greater than that of the population including normal red blood cells. That is, the population including single-ring form generally appears in region 411 in FIG. 9. The CPU 301 identifies this population including single-ring form as the third particle group.

In FIG. 8, the population including normal red blood cells appears in the region in which the forward scattered light intensity of the population including normal red blood cells is greater than that of the population including single-ring form and the population including multi-ring form. This is because particles for which the fluorescent light intensity is less than a predetermined threshold value are excluded from analysis. When particles for which the fluorescent light intensity is less than a predetermined threshold value are excluded from analysis, these particles (normal red blood cells) appear in a region of low fluorescent light intensity and forward scattered light intensity. That is, the population including single-ring form and the population including multi-ring form have the same level of forward scattered light intensity, and normal red blood cells appear in a region in which the fluorescent light intensity is lower than that of the population including single-ring form.

As shown in FIG. 8, the population including multi-ring form has the same level of forward scattered light intensity as the population including single-ring form, and has a fluorescent light intensity that is greater than the population including single-ring form. That is, the population including multi-ring form generally appears in region 412 in FIG. 9.

When the CPU 301 detects this particle group, the CPU 301 identifies the particle group as the fourth particle group.

Trophozoites and schizonts do not appear in the scattergram shown in FIG. 8. When trophozoites and schizonts appear, the appear in the region indicated by the dashed line in the drawing. That is, the population including trophozoites and schizonts have a forward scattered light intensity greater than the population including single-ring form, and fluorescent light intensity greater than that of the population including single-ring form. That is, the population including trophozoites and schizonts generally appear in region 413 in FIG. 9. When the CPU 301 detects this particle group, the CPU 301 identifies the particle group as the fifth particle group.

Figure 10:
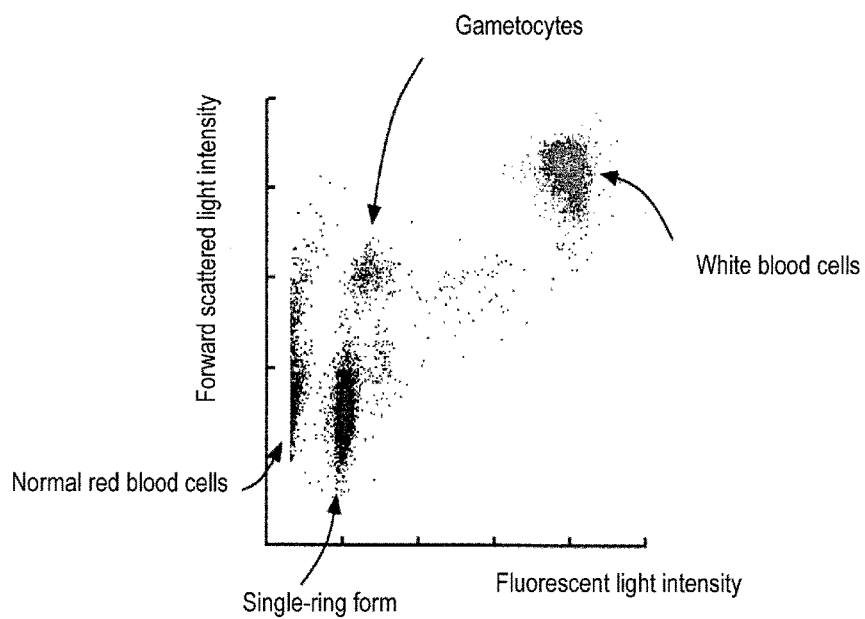
FIG. 10 shows an example of a scattergram of a blood sample infected by *Plasmodium vivax*.

FIG. 10 shows an example of a scattergram in which a population including gametocytes appears. As shown in FIG. 10, the population including gametocytes have a forward scattered light intensity greater than the population including single-ring form, and fluorescent light intensity the same level as that of the population including single-ring form. That is, the population including gametocytes generally appear in region 414 in FIG. 9. When the CPU 301 detects this particle group, the CPU 301 identifies the particle group as the sixth particle group.

Refer again to FIG. 7. The CPU 301 determines whether the number of particles belonging to the sixth particle group, that is, the number of gametocytes, is equal to or greater than a predetermined value T2 (step S404). In this case T2 is a numerical value that permits a determination that gametocytes are not present, when considering noise if the number of particles belonging to the sixth particle group is less than T2. When the number of particles belonging to the sixth particle group is equal to or greater than T2 (step S404: YES), it can be determined that gametocytes are present. In this case the CPU 301 sets the stage flag at [2] (step S405), and moves the process to step S406.

When the number of particles belonging to the sixth particle group is less than T2 (step S404: NO), it can be determined that gametocytes are not present in the blood sample. In this case, the CPU 301 moves the process to step S406.

Note that the process of determining the presence of gametocytes in step S404 also may be omitted.

The CPU 301 determines whether the number of particles belonging to the third particle group, that is, the number of single-ring form, is equal to or greater than a predetermined value T3 (step S406). In this case T3 is a numerical value that permits a determination that single-ring form are not present, when considering noise if the number of particles belonging to the third particle group is less than T3. When the number of particles belonging to the third particle group is less than T3 (step S406: NO), the CPU 301 moves the process to step S411.

When the number of particles belonging to the third particle group is equal to or greater than T3 (Step S406: YES), the CPU 301 determines whether a representative value of the forward scattered light intensity of particles belonging to the third particle group is equal to or greater than a predetermined value T4 (step S407).

Note that step S407 also may be executed without performing the process of determining the presence of single-ring form in step S406.

Figure 11:
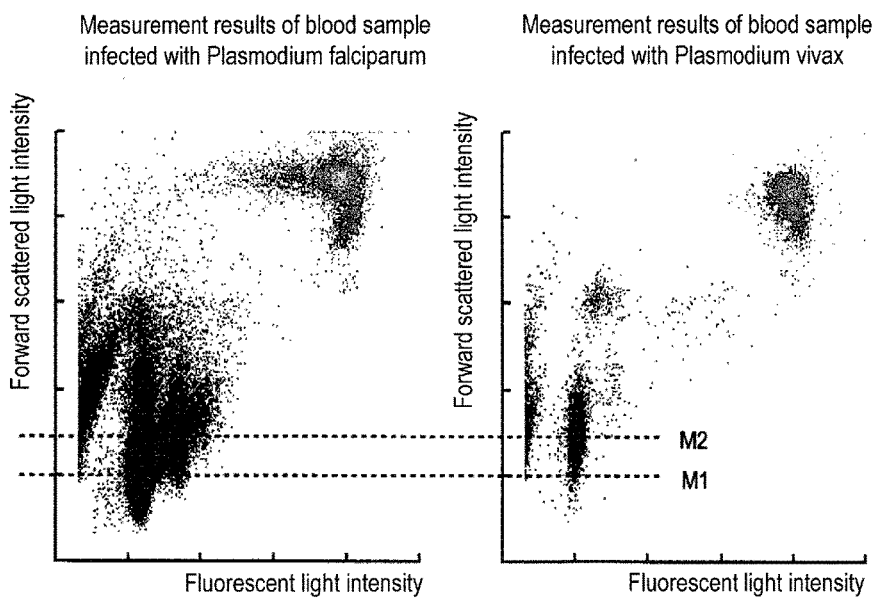
FIG. 11 illustrates a comparison of the forward scattered light intensity of single-ring form *Plasmodium falciparum* and the forward scattered light intensity of single-ring form *Plasmodium vivax*.

The size of the single-ring form *Plasmodium falciparum* is small compared to the size of single-ring forms of other species of malaria parasites. The forward scattered light intensity also reflects the size of the cell. Therefore, the population including single-ring form *Plasmodium falciparum* generally has a lower forward scattered light intensity level than that of the population including single-ring forms of other species of malaria parasites, as shown in FIG. 11. The representative value also represents a distinctive characteristic of the data group. Therefore, the representative value M1 of the forward scattered light intensity of the population including single-ring form of *Plasmodium falciparum* is smaller than the representative value M2 of the forward scattered light intensity of the population including other species of single-ring form malaria parasite. In this case T4 is a numerical value that permits discrimination between *Plasmodium falciparum* and other species of malaria parasite. According to the above, whether the malaria parasite suspected of infecting a blood sample is *Plasmodium falciparum* or another species of malaria parasite can be determined by determining whether the representative value of the forward scattered light intensity of particles belonging to the third particle group is less than, or equal or greater than T4. In this way whether a sample is infected by *Plasmodium falciparum* can be determined more accurately without affecting the number of single-ring form or multi-ring form.

The mode value, mean value, median value, or center value may be used as the representative value. Particularly the mode value is a value of most of the forward scattered light intensity in the particles belonging to the third particle group, and reflects the overall trend relating to the size of particles belonging to the third particle group. Therefore, it is preferable that the mode value is used as the representative value.

Note that a representative value of other scattered light intensities, that is, the side scattered light intensity (side scattered light peak value) or back scattered light intensity (back scattered light peak value) or the like, also may be used instead of the representative value of forward scattered light intensity.

In step S407, whether the malaria parasite suspected of infection is *Plasmodium falciparum* also can be determined based on the representative value of the forward scattered light intensity of particles belonging to the fourth particle group composed of the population including multi-ring form instead of the third particle group composed of the population including single-ring form. Whether the malaria parasite suspected of infection is *Plasmodium falciparum* also can be determined based on the representative value of the forward scattered light intensity of particles belonging to a particle group that is specified to include all ring forms by combining the single-ring form and multi-ring form.

Refer again to FIG. 7. When the representative value of the forward scattered light intensity of the third particle group is less than T4 (step S407: NO), there is a possibility of infection by *Plasmodium falciparum*. In this case the CPU 301 determines whether the number of particles belonging to the fourth particle group is equal to or greater than a predetermined value T5 (step S408). In this case T5 is a numerical value that permits a determination that multi-ring form are not present, when considering noise if the number of particles belonging to the fourth particle group is less than T5.

Multi-ring form is plentiful in the peripheral blood of persons infected with *Plasmodium falciparum*, and multi-ring form almost does not appear in the peripheral blood of persons infected with other species of malaria parasite. When the number of particles belonging to the fourth particle group is less than T5 (step S408: NO), it can be determined that multi-ring form are not present in the blood sample. In this case it cannot be said there is a high possibility that the blood sample is infected by *Plasmodium falciparum*. However, it is determined there is a possibility that the blood sample is infected with *Plasmodium falciparum* in step S407. In this case the CPU 301 sets the malaria species determination flag at [1] (step S409), ends the malaria species determination process, and returns to the measurement data analysis process.

Figure 12:
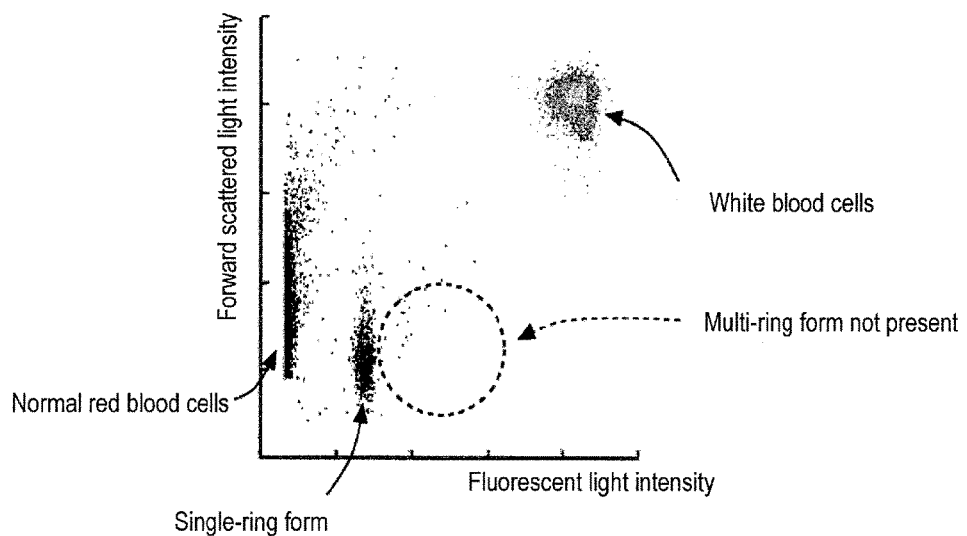
FIG. 12 shows another example of a scattergram of a blood sample infected by *Plasmodium falciparum*.

Multi-ring form sometimes may not appear, even in blood samples infected with *Plasmodium falciparum* (refer to FIG. 12). Even in the case of such blood samples, a suspicion that the blood sample is infected with *Plasmodium falciparum* can be determined by the above malaria type determination process described above.

Refer again to FIG. 7. When the number of particles belonging to the fourth particle group is equal to or greater than T5 (step S408: NO), it can be determined that there is a possibility that multi-ring form are present in the blood sample. In this case it is determined that there is a high possibility that the blood sample is infected by *Plasmodium falciparum*. In this case the CPU 301 sets the malaria species determination flag at [1] (step S410), ends the malaria species determination process, and returns to the measurement data analysis process.

Note that the process of determining the presence of multi-ring form in step S408 may be omitted. In this case the malaria species determination flag also may be set at [1] if the representative value of the forward scattered light intensity of the particles belonging to the third particle group is less than T4 in step S407.

When the representative value of the forward scattered light intensity of the particles belonging to the third particle group is equal to or more than T4 (step S407: YES), there is a possibility of infection by another species of malaria parasite. In this case the CPU 301 determines whether the number of particles belonging to the fifth particle group is equal to or greater than a predetermined value T6 (step S411). The predetermined value T6 is a standard value for determining that trophozoites and schizonts are not present when noise is considered.

Trophozoites and schizont largely do not appear in peripheral blood of persons infected with *Plasmodium falciparum*, and trophozoites and schizonts are often plentiful in peripheral blood of persons infected with other species of malaria parasite. When the number of particles belonging to the fifth particle group is less than T6 (step S411: NO), it can be determined that trophozoites and schizonts are not present in the blood sample. In this case it cannot be said there is a high possibility that the blood sample is infected by another species of malaria parasite. However, it is determined there is suspicion that the blood sample is infected with another species of malaria parasite. In this case the CPU 301 sets the malaria species determination flag at [3] (step S412), ends the malaria species determination process, and returns to the measurement data analysis process.

Figure 13:
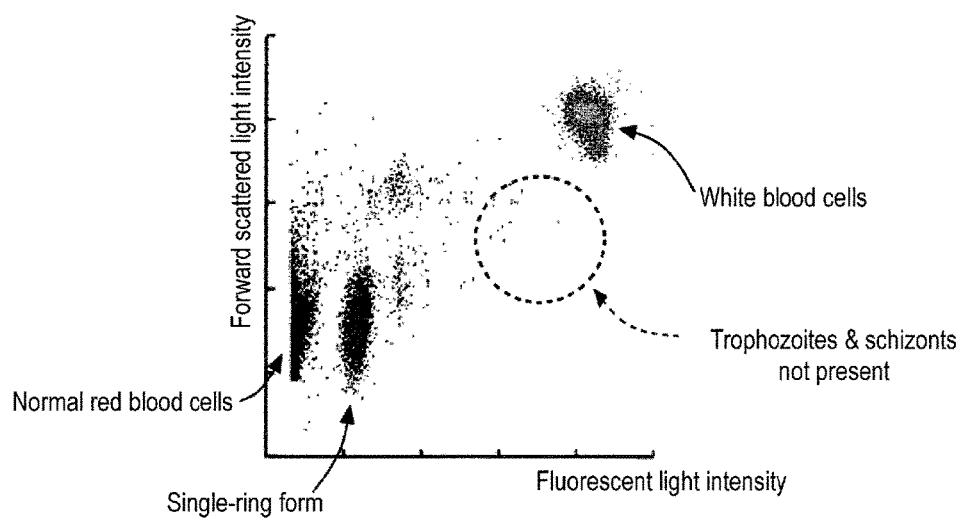
FIG. 13 shows another example of a scattergram of a blood sample infected by *Plasmodium vivax*.

Trophozoites and schizonts sometimes may not appear, even in blood samples infected with another species of malaria parasite (refer to FIG. 13). Even in the case of such blood samples, a suspicion that the blood sample is infected with another species of malaria parasite can be determined by the above malaria species determination process described above.

Refer again to FIG. 7. When the number of particles belonging to the fifth particle group is equal to or more than T6 (step S411: YES), it can be determined that trophozoites and schizonts are present in the blood sample. In this case it can be determined there is a high possibility that the blood sample is infected by another species of malaria parasite. In this case the CPU 301 sets the malaria species determination flag at [4], sets the respective stage flags at [1] (step S413), ends the malaria species determination process, and returns to the measurement data analysis process.

Figure 14:
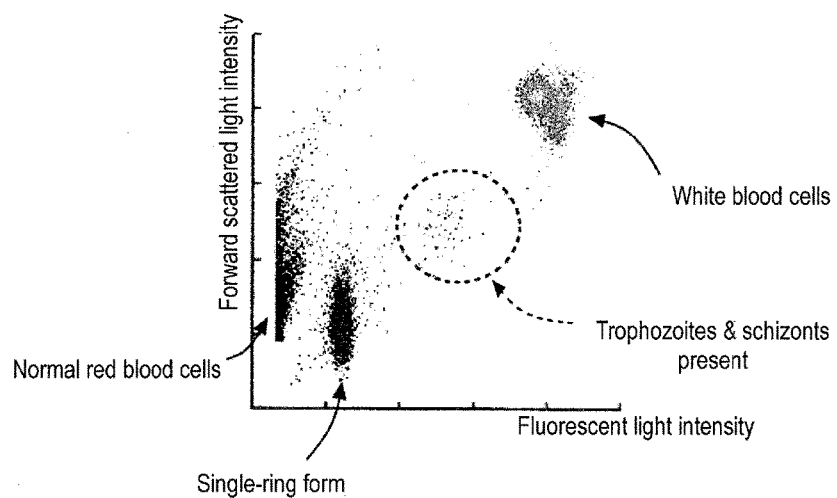
FIG. 14 shows still another example of a scattergram of a blood sample infected by *Plasmodium falciparum*.

Trophozoites and schizonts sometimes may appear, even in blood samples infected with *Plasmodium falciparum* (refer to FIG. 14). In the malaria species determination process above, the process of step S406 to determine whether a malaria parasite suspected of infection is *Plasmodium falciparum* or another species of malaria parasite is executed in priority to the process of step S409, which is the process for determining whether trophozoites and schizonts are present. Therefore, suspected infection with *Plasmodium falciparum* can be determined even in the above blood samples. Note that step S406 also may be executed after step S409 is executed.

The process of determining the presence of trophozoites and schizonts in step S411 also may be omitted. In this case the malaria species determination flag also may be set at [3] if the number of particles belonging to the third particle group is less than T3 in step S406 and the representative value of the forward scattered light intensity of particles belonging to the third particle group is equal to or greater than T4 in step S407.

Refer again to FIG. 5. When the malaria species determination process described above ends, the CPU 301 calculates the ratio (referred to as "malaria infected red blood cell ratio" below) of the number of red blood cells and number of malaria infected red blood cells (step S304). Above, the CPU 301 ends the measurement data analysis process, and returns the process to the main routine.

Refer again to FIG. 3. When the above measurement data analysis process ends, the CPU 301 outputs the analysis results to the output part 310 (step S110). Analysis results include the analysis result of red blood cell count, white blood cell count, malaria infected red blood cell count, and malaria infected red blood cell ratio, comment information such as diagnosis comments. In the malaria species determination process, information related to infection with *falciparum* malaria is output as comment information when the representative value of the forward scattered light intensity of particles belonging to the third particle group is equal to or greater than T4. That is, when the representative value of the forward scattered light intensity of particles belonging to the third particle group is less than T4 in the malaria species determining process, information indicating the possibility that the blood sample is infected with *falciparum* malaria (referred to as "*falciparum* malaria infection information" below) is output as comment information. When the representative value of the forward scattered light intensity of particles belonging to the third particle group is equal to or more than T4 in the malaria species determining process, information indicating the possibility that the blood sample is infected with another species of malaria parasite (referred to as "other species infection information" below) is output as comment information.

Specifically, the *falciparum* malaria infection information includes information indicating a high possibility that the blood sample is infected with *Plasmodium falciparum* (referred to as "first *falciparum* malaria infection information" below), and information indicating that the blood sample is suspected of infection with *Plasmodium falciparum* (referred to as "second *falciparum* malaria infection information" below). The first *falciparum* malaria infection information is output as comment information when the malaria type determination flag is set at [2], and the second *falci-*

*parum* malaria infection information is output as comment information when the malaria type determination flag is set at [1].

Other species infection information also includes information indicating a high possibility the blood sample is infected by another species of malaria parasite (referred to as "first other species infection information" below), and information indicating that the blood sample is suspected of infection with another species of malaria parasite (referred to as "second other species infection information" below). The first other species infection information is output as comment information when the malaria species determination flag is set at [4], and the second other species infection information is output as comment information when the malaria species determination flag is set at [3].

When the stage flag is set at [1], information indicating a high possibility of the presence of trophozoites and schizonts (referred to as "trophozoite/schizont information" below) is output as comment information.

When the stage flag is set at [2], information indicating a high possibility of the presence of gametocytes (referred to as "gametocyte information" below) is output as comment information.

Figure 15:
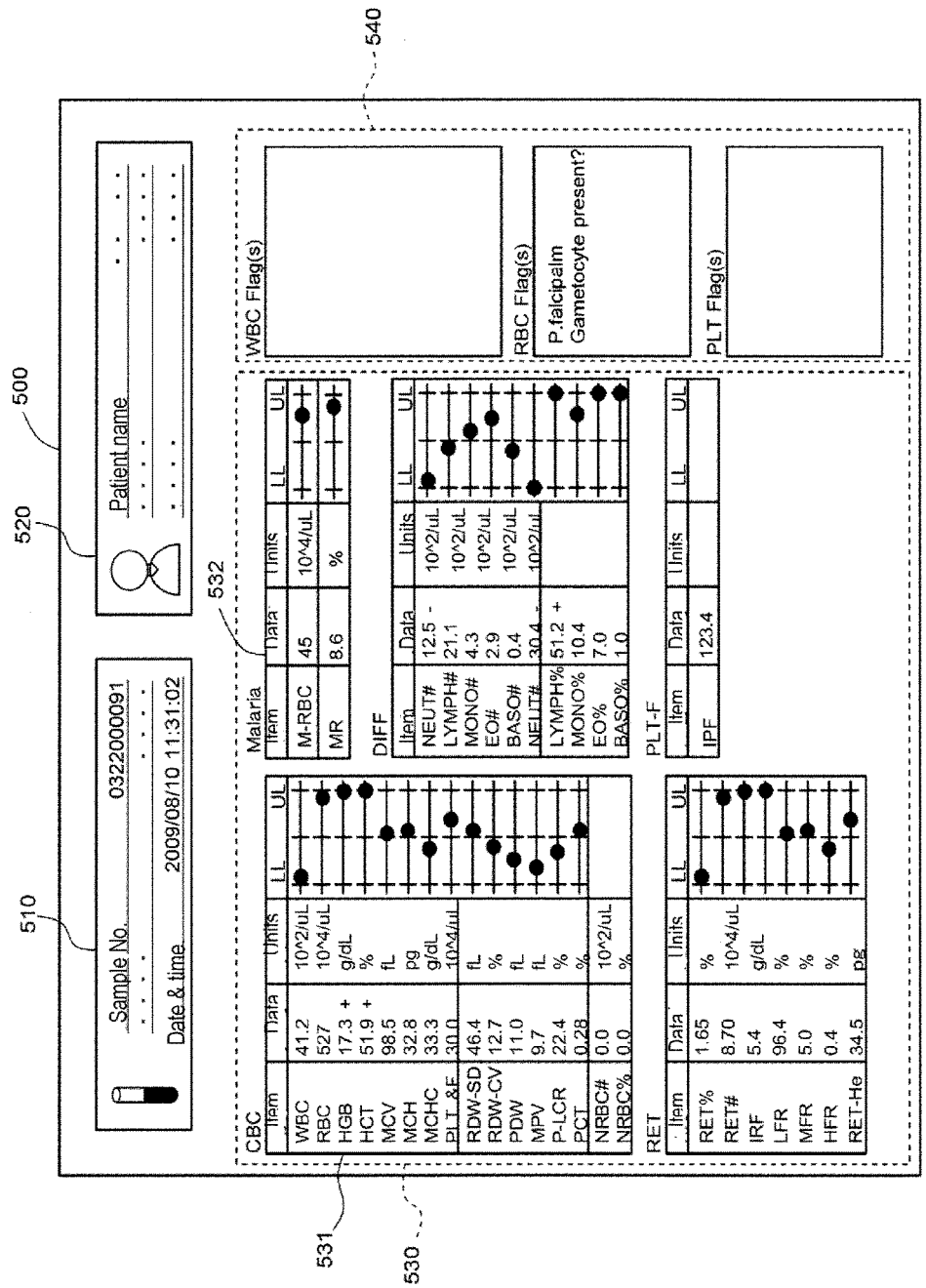
FIG. 15 shows an example of the analysis result output.

The displayed analysis results also are described referring to FIG. 15. An analysis result screen 500 is displayed on the output part 310. The analysis result screen 500 has a sample information display area 510, patient information display area 520, measurement result display area 530, and comment information display area 540. The measurement result display field 530 has a CBC item display area 531, and malaria item display area 532.

Blood sample information based on the analysis results displayed in the analysis result screen 500 is shown in the sample information display area 510. Patient information from whom the blood sample was collected is displayed in the patient information display area 520.

Measurement values of each item obtained through the measurement data analysis process are displayed in the measurement result display area 530. Measurement values of basic measurement items in blood cell analysis are displayed in the CBC item display area 531. Measurement values shown in the CBC item display area 531 include measurement values of the red blood cells (RBC) and white blood cells (WBC). Measurement values of measurement items related to malaria infected red blood cells are shown in malaria item display area 532. Measurement values shown in the malaria item display area 532 include measurement values of the malaria infected red blood cell count (M-RBC) and malaria infected red blood cell ratio (MR).

Comment information for the user is displayed in the comment information display area 540 when the obtained results must be reported to the user, such as suspected infection with malaria parasite, through the measurement data analysis process. The first *falciparum* malaria infection information, "*P. falciparum*", is displayed in the comment information display area 540 when the malaria type determination flag is set at [2] in the measurement data analysis process, and the second *falciparum* malaria infection information, "*P. falciparum*", is displayed in the comment information display area 540 when the malaria type determination flag is set at [1] in the measurement data analysis process. Note that the first *falciparum* malaria infection information is not limited to the above, inasmuch as the information may indicate a high possibility that the blood sample is infected with *Plasmodium falciparum*. The second *falciparum* malaria infection information is not limited to the above, inasmuch as the information may indicate the blood sample is suspected of infection with *Plasmodium falciparum*. The same information indicating a possibility that the blood sample is infected with *Plasmodium falciparum* also may be output when the malaria type determination flag is set at either [1] or [2].

The first other species infection information, "Other species", is displayed in the comment information display area 540 when the malaria species determination flag is set at [4] in the measurement data analysis process, and the second other species infection information, "Other species?", is displayed in the comment information display area 540 when the malaria type determination flag is set at [3] in the measurement data analysis process. Note that the first other species infection information is not limited to the above, inasmuch as the information may indicate a high possibility that the blood sample is infected with another species of malaria parasite. The second other species infection information is not limited to the above, inasmuch as the information may indicate the blood sample is suspected of infection with another species of malaria parasite. The same information indicating a possibility that the blood sample is infected with another species of malaria parasite also may be output when the malaria species determination flag is set at either [3] or [4].

The trophozoite and schizont information, "Trophozoite/schizont present", is displayed in the comment information display area 540 when the stage flag is set at [1] in the measurement data analysis process. Trophozoites and schizonts appear in stages progressing from the ring form in the life cycle of the malaria parasite. Therefore, the user can be notified that infection of the person is at the trophozoite or schizont presence stage by outputting the trophozoite/schizont information when trophozoites or schizonts are detected.

The gametocyte information, "Gametocyte present?", is displayed in the comment information display area 540 when the stage flag is set at [2] in the measurement data analysis process. Gametocytes appear in stages progressing from the stage at which trophozoites and schizonts are present. In malaria infection, gametocytes may be present in the blood even when the symptoms are alleviated. Therefore, it is important to eliminate gametocytes in the treatment of malaria infection. The user can be notified of the stage at which gametocytes appear by outputting gametocyte information when gametocytes are detected.

What is claimed is:

1. A blood analyzer comprising:
    a sample preparing part comprising a reaction tank in which a blood sample, a staining dye to stain a nucleic acid, and diluent to contract red blood cells are mixed and measurement sample is prepared;
    a detecting part comprising a plurality of sensors configured to detect a fluorescent light intensity and a scattered light intensity given off from the measurement sample irradiated with light;
    a display; and
    a memory and a processor executing a computer program stored in the memory, wherein the processor is programmed to identify a population including red blood cells infected by single ring-form malaria parasite based on the fluorescent light intensity and the scattered light intensity, and output to display information relating to infection of *Plasmodium falciparum* based on a scattered light intensity distribution of particles associated with the identified population that includes red blood cells infected by the single ring-form malaria parasite.

2. The blood analyzer of claim 1, wherein
the processor is programmed to identify the population including red blood cells infected by the ring-form malaria parasite based on the fluorescent light intensity and the scattered light intensity, and output to the output part the information relating to infection of *Plasmodium falciparum* based on the scattered light intensity distribution of particles belonging to the identified population that includes red blood cells infected by the ring-form malaria parasite.

3. The blood analyzer of claim 1, wherein
the population including red blood cells infected by the ring-form malaria parasite is a third particle group in which the scattered light intensity is less than that of a first particle group of the population including white blood cells, and the fluorescent light intensity is less than that of the first particle group and greater than that of a second particle group of the population including red blood cells not infected by malaria parasite.

4. The blood analyzer of claim 3, wherein
the processor is programmed to output to the output part the information relating to infection of *Plasmodium falciparum* based on a representative value of the scattered light intensity of particles belonging to the third particle group.

5. The blood analyzer of claim 4, wherein
the processor is programmed to output to the output part information relating to infection of *Plasmodium falciparum* based on the mode value of the scattered light intensity of particles belonging to the third particle group.

6. The blood analyzer of claim 4, wherein
the processor is programmed to output to the output part information indicating a possibility of infection of the blood sample by *Plasmodium falciparum* when the representative value is less than a predetermined value.

7. The blood analyzer of claim 6, wherein
the processor is programmed to output to the output hardware information indicating a possibility of infection of the blood sample by a malarial parasite other than *Plasmodium falciparum* when the representative value is equal to or greater than the predetermined value.

8. The blood analyzer of claim 7, wherein
the processor is programmed to identify a fifth particle group in which the scattered light intensity is greater than that of the third particle group and the fluorescent light intensity is greater than that of the third particle group when the representative value is equal to or greater than the predetermined value, and output to the output hardware information indicating a high probability of infection of the blood sample by a malarial parasite other than *Plasmodium falciparum* when the number of particles belonging to the fifth particle group is equal to or greater than a third predetermined value.

9. The blood analyzer of claim 8, wherein
the processor is programmed to output to the output hardware information indicating suspicion that the blood sample is infected by a malarial parasite other than *Plasmodium falciparum* when the number of particle belonging to the fifth particle group is less than the third predetermined value.

10. The blood analyzer of claim 9, wherein
the processor is programmed to output to the output hardware information indicating a possibility of trophozoites or schizonts in the blood sample when the number of particle belonging to the fifth particle group is equal to or greater than the third predetermined value.

11. The blood analyzer of claim 6, wherein
the processor is programmed to identify a fourth particle group in which the scattered light intensity is the same as that of the third particle group and the fluorescent light intensity is greater than that of the third particle group when the representative value is less than a predetermined value, and output to the output hardware information indicating a possibility of infection of the blood sample by *Plasmodium falciparum* when the number of particles belonging to the fourth particle group is equal to or greater than a second predetermined value.

12. The blood analyzer of claim 11, wherein
the processor is programmed to output to the output part information indicating suspicion that the blood sample is infected by *Plasmodium falciparum* when the number of particle belonging to the fourth particle group is less than the second predetermined value.

13. The blood analyzer of claim 3, wherein
the processor is programmed to identify a sixth particle group in which the scattered light intensity is greater than that of the third particle group and the fluorescent light intensity is the same as the third particle group, and output to the output hardware information indicating there is a possibility of gametocytes appearing in the blood sample based on the number of particles belonging to the sixth particle group.

14. The blood analyzer of claim 3, wherein
the processor is programmed to identify a seventh particle group in which the scattered light intensity is less than that of the first particle group and the fluorescent light intensity is greater than that of the second particle group, and output to the output part the number of particles belonging to the seventh particle group.

15. The blood analyzer of claim 14, wherein
the sample preparing part is configured to prepare a second measurement sample by mixing the blood sample and a second diluent that is different from the previous diluent;
further comprising:
a second detecting part configured to detect the electrical resistance of each particle contained in the second measurement sample prepared by the sample preparing hardware;
the processor is programmed to detect the red blood cells contained in the second measurement sample based on the electrical resistance detected by the second detecting part, and output to the display the ratio of the number of detected red blood cells and the number of particles contained in the seventh particle group.

16. The blood analyzer of claim 1, further comprising:
a flow cell configure to flow the measurement sample prepared by the sample preparing part;
a light source configured to irradiate blue-violet laser light on the measurement sample flowing through the flow cell;
wherein the processor is programmed to detect the fluorescent light intensity and scattered light intensity obtained when the blue-violet laser light from the light source irradiates the measurement sample flowing through the flow cell.

* * * * *